(12) United States Patent
Troy et al.

(10) Patent No.: US 10,105,837 B2
(45) Date of Patent: *Oct. 23, 2018

(54) TRACKING ENABLED EXTENDED REACH TOOL SYSTEM AND METHOD

(71) Applicant: The Boeing Company, Chicago, IL (US)

(72) Inventors: James J. Troy, Isssaquah, WA (US); Gary E. Georgeson, Tacoma, WA (US); Paul S. Rutherford, Maple Valley, WA (US); Nathan R. Smith, Melbourne, FL (US)

(73) Assignee: The Boeing Company, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/358,541

(22) Filed: Nov. 22, 2016

(65) Prior Publication Data

US 2017/0072557 A1    Mar. 16, 2017

Related U.S. Application Data

(63) Continuation-in-part of application No. 13/750,565, filed on Jan. 25, 2013, now Pat. No. 9,513,231.

(51) Int. Cl.
*H04N 7/18* (2006.01)
*B25J 1/02* (2006.01)
(Continued)

(52) U.S. Cl.
CPC .......... *B25J 1/02* (2013.01); *B23Q 17/2233* (2013.01); *B25J 1/08* (2013.01); *B25J 15/00* (2013.01);
(Continued)

(58) Field of Classification Search
CPC ..... G01N 21/954; G01N 21/956; H04N 7/183
(Continued)

(56) References Cited

U.S. PATENT DOCUMENTS

| 5,000,533 | A | 3/1991 | Gerwers |
| 5,757,419 | A | 5/1998 | Qureshi et al. |

(Continued)

FOREIGN PATENT DOCUMENTS

| CN | 202258269 | 5/2012 |
| DE | 10 2010 010419 | 9/2011 |

(Continued)

OTHER PUBLICATIONS

Georgeson, G. et al., "Surgical NDE (SuNDE) Tool for Limited Access Inspection," presented at the ASNT Fall Conference, Oct. 24-27, 2011.

(Continued)

*Primary Examiner* — Michael Lee
*Assistant Examiner* — Jean W Desir
(74) *Attorney, Agent, or Firm* — Vivacqua Law

(57) ABSTRACT

An extended-reach tool system may include a gimbal positioned adjacent a surface opening; an extended-reach arm having a tool and engaging the gimbal; a sensor system for measuring a position of the arm relative to the gimbal and a position and spatial orientation of the tool relative to the opening; a computer control that converts one or both of the rotational and linear measurements from the sensor system into spatial location representations for virtual representations of 3-D models of the workpiece and tool, determines a position and orientation of the tool relative to the opening and workpiece, and adjusts the virtual representations of the 3-D models of the workpiece and tool as the arm and tool move relative to the workpiece, representing a real-time orientation of the tool relative to the workpiece; and a (Continued)

display for displaying the virtual representations of the 3-D models of the workpiece and tool.

11 Claims, 9 Drawing Sheets

(51) Int. Cl.
*B25J 1/08* (2006.01)
*B25J 15/00* (2006.01)
*B23Q 17/22* (2006.01)
*G06T 19/20* (2011.01)
*G06T 19/00* (2011.01)
*G01N 21/954* (2006.01)

(52) U.S. Cl.
CPC ......... *G01N 21/954* (2013.01); *G06T 19/003* (2013.01); *G06T 19/006* (2013.01); *G06T 19/20* (2013.01); *G06T 2219/2004* (2013.01)

(58) Field of Classification Search
USPC .......... 348/92, 94, 95, 180, 82, 85; 73/866.5
See application file for complete search history.

(56) References Cited

U.S. PATENT DOCUMENTS

| | | | |
|---|---|---|---|
| 6,705,871 B1 * | 3/2004 | Bevirt | G05G 9/04 345/156 |
| 7,114,406 B2 | 10/2006 | Wright et al. | |
| 8,109,160 B2 | 2/2012 | Bossi et al. | |
| 9,513,231 B2 * | 12/2016 | Smith | G01N 21/954 |
| 2005/0073673 A1 | 4/2005 | Devitt et al. | |
| 2005/0199832 A1 | 9/2005 | Twerdochlib | |
| 2006/0066847 A1 | 3/2006 | Penza | |
| 2008/0204864 A1 * | 8/2008 | Sander | G02B 21/0012 359/368 |
| 2009/0180110 A1 | 7/2009 | Drost et al. | |
| 2009/0196459 A1 | 8/2009 | Watt et al. | |
| 2010/0024559 A1 | 2/2010 | Bossi et al. | |
| 2012/0147173 A1 | 6/2012 | Lynch | |

FOREIGN PATENT DOCUMENTS

| | | |
|---|---|---|
| JP | 61-256316 | 11/1986 |
| JP | 10-128688 | 5/1998 |
| WO | 2008/034144 | 3/2008 |

OTHER PUBLICATIONS

Georgeson, G. et al., "Surgical NDE (SuNDE)," AFRL-RX-WP-TR-2011-XXXX, Final Report, Jun. 2011.

Machine translation of the description of DE 10 2010 010 419 A1 (Sep. 8, 2011).

EP, Search Report and Opinion, European Application No. 13194549.5, dated May 16, 2014.

U.S. Non-Final Office Action; U.S. Appl. No. 13/750,565 (dated Aug. 31, 2015).

U.S. Final Office Action; U.S. Appl. No. 13/750,565 (dated Apr. 19, 2016).

U.S. Advisory Action; U.S. Appl. No. 13/750,565 (dated Jul. 18, 2016).

U.S. Notice of Allowance; U.S. Appl. No. 13/750,565 (dated Jul. 29, 2016).

CN, English translation of Office Action and Search Report, Chinese Patent Application No. 201310629819X, 11 pages (dated Jul. 14, 2017).

CN, Second Office Action with English translation, Chinese Patent Application No. 201310629819X, 8 pages (dated Mar. 27, 2018).

EP, Communication pursuant to Article 94(3) EPC, European Patent Application No. 13194549.5, 4 pages (dated Feb. 22, 2018).

* cited by examiner

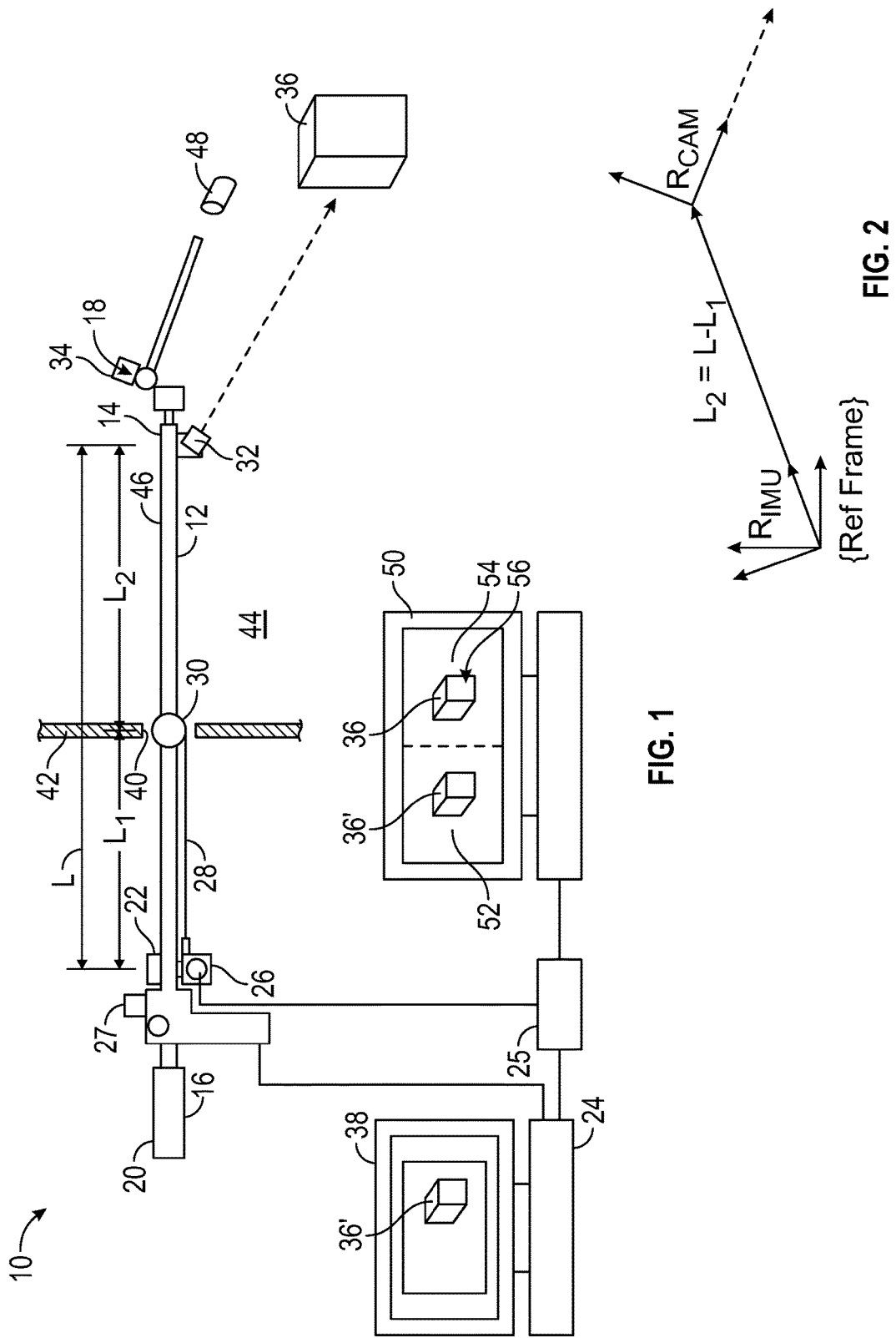

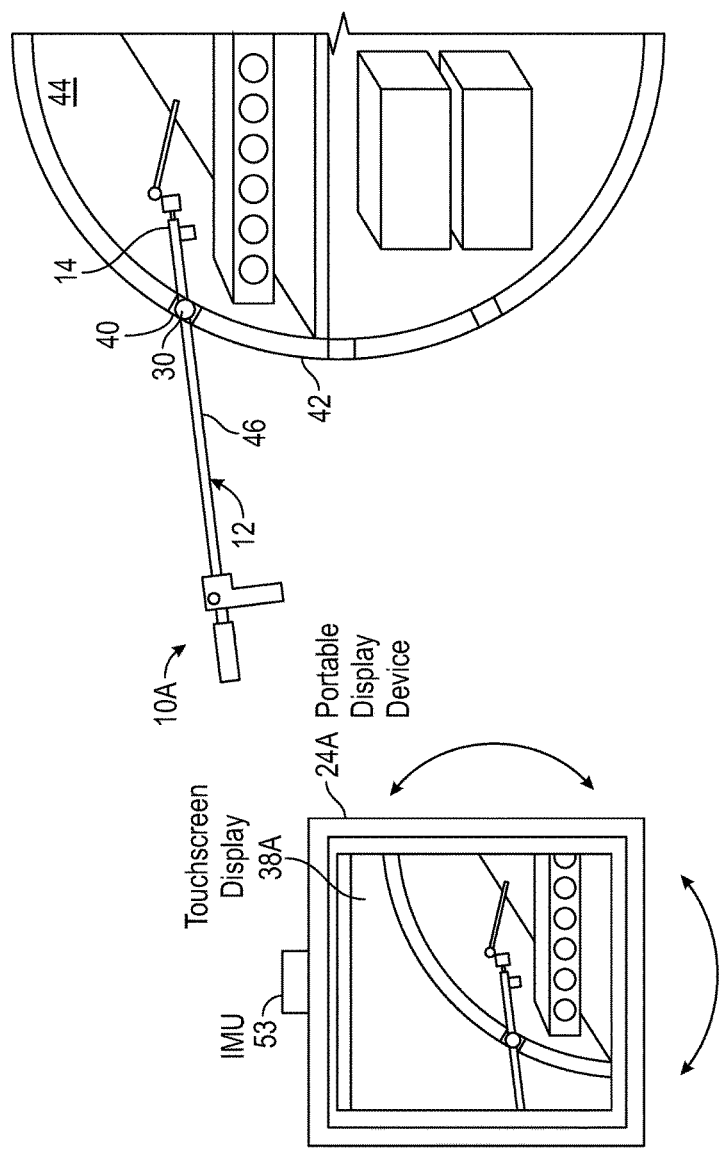

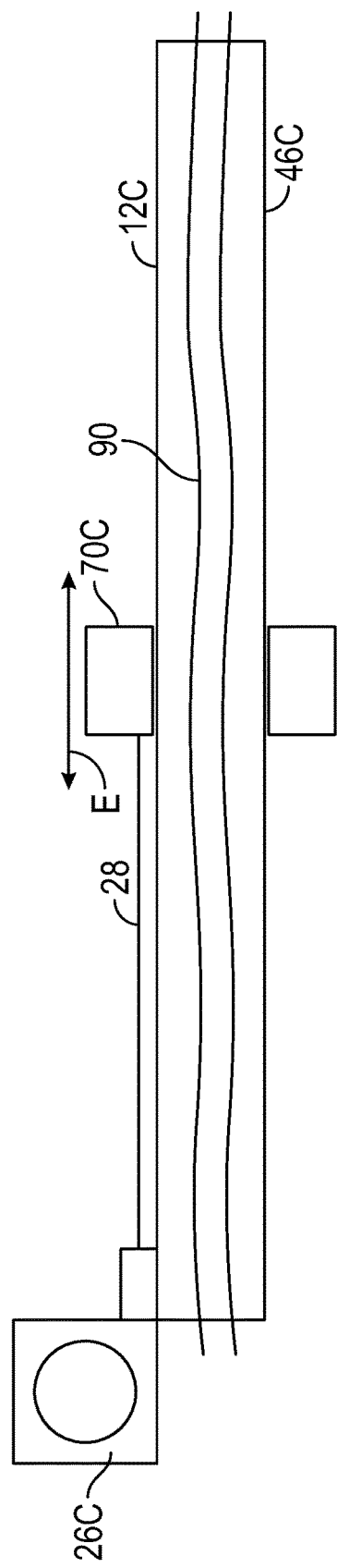

TRACKING ENABLED EXTENDED REACH TOOL SYSTEM AND METHOD

FIELD

The disclosure relates to systems and methods for using tools to perform tasks beyond line of sight and in limited access areas, and more particularly, for systems and methods utilizing an instrumented arm equipped with an end effector in the form of a tool.

BACKGROUND

Once a vehicle, such as an aircraft, has been placed in service, it may be necessary to periodically inspect and, if necessary repair or replace the components of the vehicle periodically. Such components may take the form of discrete electronic components, hydraulic components, wires and cables, other fittings, and bulkheads. Many of the components may be partially or entirely located within sealed enclosures on the vehicle. If a workpiece, such as one of these components, is located within a sealed enclosure or other limited-access area, the disassembly and reassembly of the structure surrounding the workpiece may be necessary in order to perform inspection, repair, or other actions, which is costly and time consuming.

As an alternative, structure, such as walls, enclosing such limited-accessed areas may include an access opening sized to receive a sensor, tool, or other instrument that enables a visual inspection of, or an operation to be performed on, the workpiece. If the interior of the structure surrounding the workpiece is relatively open, use of such a sensor, tool, or other instrument may be guided visually by a user. However, in many applications, such an enclosure may include an interior in which the workpiece may be obstructed by hardware or other structure that makes access and inspection difficult. Further, in such limited-access areas, the workpiece may be occluded by smoke, dust, or liquid, making it difficult to inspect or effect repair or replacement.

For example, certain internal aircraft structures may require in-service inspection, maintenance, and repair, but such structures may be obstructed by tubes, brackets and actuators that must be removed first. In some cases, initial inspections may take more than 1000 hours, and subsequent inspections may take more than 500 hours. Other internal aircraft components may be obstructed by other structural elements. Because of structural removal issues, an initial aircraft inspection may take more than 2000 hours, and recurring inspections as much as 1100 hours.

Typically, inspections may be performed using borescopes and remote cameras shaped to be inserted into limited access areas. Such devices may be able to see surface flaws or damage, but not subsurface damage. In many cases, features found using these devices and methods may be misdiagnosed as damage, and only determined to be benign markings after costly disassembly. Fatigue inspections of titanium attach fittings on aircraft may be programmed as visual borescope inspections, but if crack-like indications are found, there is no current method of confirming them other than simply disassembly of the structure.

With the increase in use of bonded and co-cured composite structures for aircraft, access to the interior for production and in-service inspection may be very difficult, costly, and time-consuming. Such inspection may be so expensive that certain lower-cost structure designs cannot be utilized because of the high cost of performing in-service inspections.

In addition, once a defect has been detected in such an enclosure, it may be necessary to effect repair. Typically, it is necessary either to enlarge the inspection opening, which may require removal of material or removal of a larger access plate, in order to perform a repair at the location of the defect. Such repair operations may be expensive due to the additional labor and cost of removal of structure in order to access the area of the defect.

Accordingly, there is a need for a system and method for nondestructive inspection in limited, enclosed areas that tracks the position and orientation of an inspection device in a confined space. There is also a need for utilizing tools in such limited enclosed areas to effect maintenance and/or repair without requiring enlarging the access opening, and without providing an operator with line-of-sight vision of the workpiece.

SUMMARY

The present disclosure describes a tracking-enabled extended-reach tool system and method for acting upon a workpiece located in a limited-access area or enclosure that does not rely on line-of-sight vision of the workpiece by an operator. In an embodiment, a tracking-enabled extended-reach tool system for acting upon a workpiece includes a gimbal adapted to be positioned adjacent an opening in a surface; an extended-reach arm having a first end and a second end, and an end effector including a tool adjacent the first end, the extended-reach arm engaging the gimbal for relative rotational movement and relative slidable movement through the opening such that the end effector and tool are positioned on a side of the surface opposite the second end; a sensor system for measuring gimbal and end effector rotations, a linear position of the extended-reach arm relative to the gimbal, and one or both of a position and a spatial orientation of the tool relative to the opening; a computer control connected to receive rotational and linear measurements from the sensor system, convert the rotational and the linear measurements into spatial location representations for virtual representation of three-dimensional (3-D) models of the workpiece and the tool, determine one or both of the position and the orientation of the tool relative to the opening and to the workpiece, and adjust the virtual representations of the 3-D models of the workpiece and the tool as the extended-reach arm and tool move relative to the workpiece, thereby representing a real-time orientation of the tool relative to the workpiece; and a display for displaying the virtual representations of 3-D models of the workpiece and the tool from the computer control in real time.

In another embodiment, a method for acting upon a workpiece with a tracking-enabled extended-reach tool system includes positioning a gimbal adjacent an opening in a surface; engaging the gimbal with an extended-reach arm having a first end and a second end, and an end effector including a tool adjacent the first end, the extended-reach arm engaging the gimbal for relative rotational movement and relative slidable movement through the opening such that the end effector and tool are positioned on a side of the surface opposite the second end; measuring gimbal and end effector rotations, a linear position of the extended-reach arm relative to the gimbal, and one or both of a position and a spatial orientation of the tool relative to the opening with a sensor system; receiving rotational and linear measurements from the sensor system, converting the rotational and the linear measurements into spatial location representations for virtual representation of 3-D models of the workpiece and the tool, determining one or both of the position and the orientation of the tool relative to the opening and to the workpiece, and adjusting the virtual representations of the 3-D models of the workpiece and the tool as the extended-reach arm and tool move relative to the workpiece by a computer control, thereby representing a real-time orientation of the tool relative to the workpiece; displaying the virtual representations of the 3-D models of the workpiece and the tool from the computer control on a display; and manipulating the extended-reach arm to act upon the workpiece with the tool.

In yet another embodiment, a tracking-enabled extended-reach tool system for acting upon a workpiece includes a gimbal adapted to be positioned adjacent an opening in a surface; an extended-reach arm having a first end and a second end, and an end effector including a tool adjacent the first end, the extended-reach arm engaging the gimbal for relative rotational movement and relative slidable movement through the opening such that the end effector and tool are positioned on a side of the surface opposite the second end; a sensor system for measuring a linear position of the extended-reach arm relative to the gimbal, and one or both of a position and a spatial orientation of the tool relative to the opening; a computer control connected to receive signals from the sensor system indicative of a linear position of the extended-reach arm relative to the gimbal and one or both of the position and the spatial orientation of the tool relative to the opening, and to determine one or both of the position and the orientation of the tool relative to the opening and to the workpiece in real time; and a display for displaying a representation of the workpiece and the tool relative to each other from the computer control in real time.

Other objects and advantages of the disclosed tracking-enabled extended-reach tool system and method will be apparent from the following description, the accompanying drawings and the appended claims.

BRIEF DESCRIPTION OF THE DRAWINGS

FIG. 1 is a schematic representation of an embodiment of the disclosed tracking-enabled extended-reach tool system;

FIG. 2 is a diagram showing the position vectors of the camera and inertial measurement unit of the tracking-enabled extended-reach tool system of FIG. 1:

FIG. 3 is another embodiment of the disclosed tracking-enabled extended-reach tool system;

FIGS. 5A, 5B and 5C are schematic representations of different embodiments of the extended-reach arm of the disclosed tracking-enabled extended-reach tool system;

DETAILED DESCRIPTION

Figure 4B:
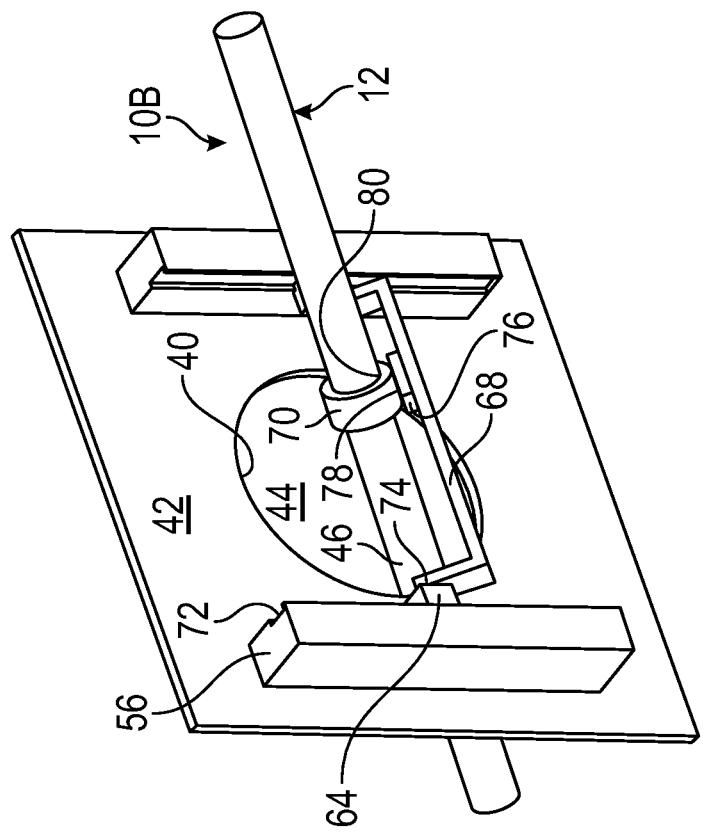
FIGS. 4A and 4B are details of an embodiment of the disclosed tracking-enabled extended-reach tool system.

As shown in FIG. 1, the disclosed tracking-enabled extended-reach tool system, generally designated 10, may include an extended-reach arm 12 having a first end 14, and a second end 16. The first end 14 may include an end effector, generally designated 18, that may include a tool. The second end 16 may include a handle 20 shaped to be grasped and manipulated by a user (not shown). The extended-reach arm 12 may include a sensor system, which in the embodiment of FIG. 1 may include an inertial measurement unit (IMU) 22 that may be connected to a computer control, generally designated 24, and an encoder reading device 25.

The sensor system also may include string encoder 26. The string encoder 26 may communicate with the encoder reading device 25 and have a cable 28 attached to a gimbal, which in the embodiment of FIG. 1 may take the form of a slider ball 30 mounted on the extended-reach arm 12. Thus, the string encoder 26 may measure the linear position of the extended-reach arm 12 relative to the slider ball 30. Optionally, or in addition to string encoder 26, a laser measurement device (LMD) 27 may be mounted on the handle 20 of the extended-reach arm 12. As will be described in detail, both string encoder 26 and LMD 27 may be used by computer control 24 to determine the length of the extended-reach arm 12 that is beyond the slider ball 30, in order to locate the end of the extended-reach arm.

The extended-reach arm 12 also may include a camera 32 mounted adjacent the first end 14, and a second laser measurement device (LMD) 34. The camera 32 may be connected to the computer control 24, either by wires or wirelessly, so that an object 36 viewed by the camera may appear on a display 38.

The extended-reach arm 12 generally may be elongate in shape and sized such that the first end 14 may be inserted through an access opening 40 in a surface, which may take the form of wall 42, so that the first end 14 may be placed in an enclosed inspection space 44 (see also FIG. 3) on a side of wall 42 opposite the second end 16 and handle 20. In embodiments, the surface may include or be a part of a bulkhead, a door, a floor, a panel, or any other enclosure that may have an access opening in it to receive the gimbal.

The slider ball 30 may be positioned adjacent the access opening 40, and attached to or otherwise fixed relative to the wall 42. Since the IMU 22 is mounted on the extended-reach arm 12, it tracks the orientation of the extended-reach arm of the tool system 10, which may be equivalent to tracking orientation for any part of the tool that may be rigidly attached to the shaft 46 of the extended-reach device. Signals generated by the IMU 22 indicative of the orientation of the shaft 46 may be received by the computer control 24.

With the embodiment of FIG. 1, the data from IMU 22 may be used to measure orientation of shaft 46. The distance measurement of the shaft relative to the access opening 40 may be acquired from a variety of sources, such as the string encoder 26. Alternately, or in addition, the end effector 18 may utilize the LMD 34 to track the insertion of the end effector device 18 relative to a known reference object 48.

As shown in FIGS. 1 and 2, with this tool system 10, the result of data input from the IMU 22, and the string encoder 26 and/or the LMD 34 may be a 4×4 homogenous transformation matrix that encodes the position and orientation of the first end 14 of the shaft 46 of the end-effector 18 relative to a reference coordinate system, designated $R_{IMU}$, shown in FIG. 2. The coordinate system of the camera 32 is designated $R_{CAMERA}$ in FIG. 2. The reference frame of the camera 32, $R_{CAMERA}$, will remain fixed relative to the reference frame of the IMU 22, $R_{IMU}$ because both the IMU and camera are mounted on the shaft 46. Consequently, the orientation of the IMU 22, which may be communicated to the computer control 24, will indicate the orientation of the camera 32.

The distance L from the IMU 22 to the camera 32 (which is a known distance) is expressed as the sum of the distance $L_1$ from the IMU to the slider ball 30, which is indicative of the distance from the IMU to the wall 42, and the distance $L_2$ from the slider ball 30 to the camera 32. Accordingly, the distance from the inspection opening 40 to the object 36 viewed by the camera 32 may be expressed as the difference between the total length L and the length $L_1$ from the IMU 22 to the inspection opening 40. This distance may also be calculated or determined by measuring the distance from the LMD 34 to a known reference object 48 within the interior 44. These measurements may be updated continuously in real time as the extended-reach arm 12 is manipulated by an operator (not shown).

In an embodiment, a three-dimensional (3-D) visualization application may be used to show on display 38 a CAD-based display of the virtual environment in the field of view of the camera 32. The 3-D virtual environment may be used to help guide the user and keep track of the inspection sequence. For example, locations of specific areas of interest may be highlighted in one color, while areas that have been inspected, and/or may still need to be inspected, may be shown in other colors. In addition, a virtual representation of the arm 12 may be shown operating in a virtual environment as well (see, e.g., FIG. 3), since the position and orientation of the tool are known from the tracking instrumentation (IMU 22, string encoder 26, and LMD 34).

Accordingly, as shown in FIG. 1, as camera 32 views object 36, the display 38 may show a virtual representation 36' of the object 36 that is generated by the 3-D visualization application. If the LMD 34 is utilized, the distance data it provides may be used with the relative orientation of the end effector 18 to create a transformation matrix to post-multiply the transformation of the shaft 46. This provides the location of the laser intersection point with the object 36, and is computed in the same manner as the relative camera view transformation described above.

The 3-D visualization application has an architecture that allows external applications to modify the position and orientation information for the virtual camera or other objects in the 3-D environment. In some applications this may be accomplished using a plug-in framework that has an application programming interface (API) to allow control of the visualization environment from a separate application.

In an embodiment, the tool system 10 may include a display 50, which may be used in addition to or instead of display 38. This display 50 may show a virtual representation 52 of the object 36' alongside an actual camera representation 54 of the object 36. This side-by-side display may enable a user to compare the actual object 36 with the virtual object 36', which may enable the operator to detect a defect 56 or other problem with the viewed object. Data and representations of the object 36 and known reference object 48, as well as the contours and other objects in the inspection space 44 that may enable the 3D visualization application to display virtual representations 36', may move as the camera 32 moves with movement of the extended-reach arm 12, may be stored in a database that may be part of computer control 24, or may be accessed by computer control from a remote location (not shown).

As shown in FIG. 3, in another embodiment, which may or may not be used in combination with the embodiment shown in FIG. 1, a portable display device 24A, such as a tablet PC (shown), which may be a touch screen-enabled tablet, a smartphone, DisplayLink monitor, a wearable, a hand-held device, or a heads-up display, may be equipped with a separate IMU 53 and used to provide virtual viewpoint orientation control. The virtual viewpoint location may be linked to the fixed location of the access port 40, or any location associated with the tool 10A, for example, the first end 14 of the tool. Consequently, any rotation, pivoting or angling of the display device 24A and IMU 53 will result in a corresponding rotation, pivoting or angling of the virtual representation 38A. This capability may allow for a more intuitive interface and provide improved situational awareness for the user. If the display device 24A is equipped with a touchscreen display 38A, objects may selected on the screen and positions recorded for further analysis.

Figure 4A:
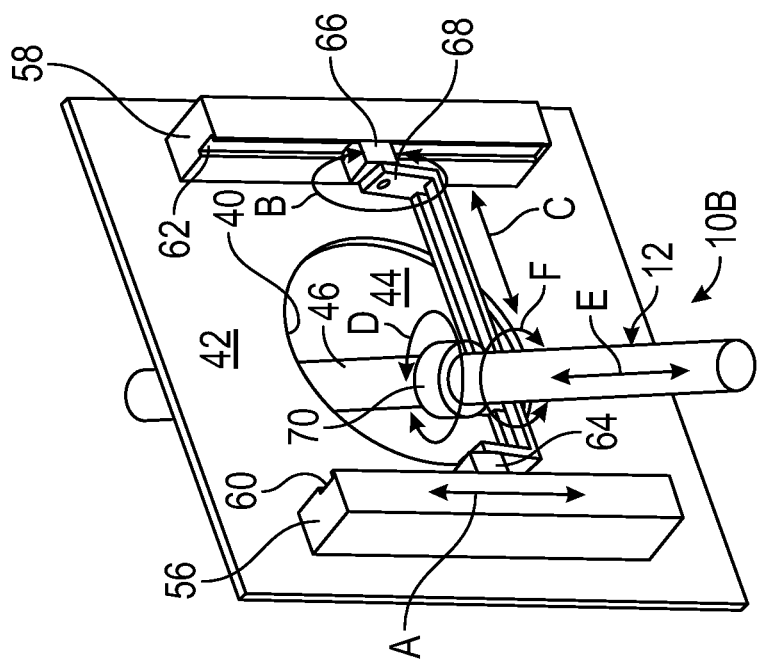

Another embodiment of the multi-axis tool 10B is shown in FIGS. 4A and 4B. With this embodiment, the sensor system, which in the embodiment of FIG. 1 included IMU 22 and slider ball 30, may be replaced or augmented by a system of linear and rotational encoders used to track movements of the extended-reach arm 12. The multi-axis tool 10B may include a gimbal that includes parallel slides 56, 58, blocks 64, 66, rail 68, and sliding attachment ring 70 positioned adjacent the opening 40 in the wall 42.

Parallel slides 56, 58 may extend in length and may be attached to the wall 42 by means such as clamps, suction cups, screws and the like (not shown) on either side of inspection opening 40. Slides 56, 58 may include longitudinal slots 60, 62, respectively, that receive blocks 64, 66 for relative slidable movement in the direction of arrow A. The rail 68 may be attached to the blocks 64, 66 for relative rotational movement in the direction of arrow B. The rail 68 may extend between the slides 56, 58 across inspection opening 40. The sliding attachment ring 70 may be mounted on the rail 68 for relative slidable or translational movement in the direction of arrow C, and be mounted for pivotal movement in the direction of arrow D (i.e., about an axis normal to the rail 68) on the rail. Further, the shaft 46 of extended-reach arm 12 may engage the sliding attachment ring 70 for relative slidable movement in the direction of arrow E, and relative rotational movement in the direction of arrow F.

As shown in FIG. 4B, slide 56 may include a linear encoder 72 to transmit a signal indicative of the position of block 64 relative to slide 56 in the direction of arrow A (FIG. 4A), and block 64 may include a rotational encoder 74 that may transmit a signal indicative of the relative rotation angle of rail 68 to block 64 in the direction of arrow B (FIG. 4A). Rail 68 may include a linear encoder 76 that may transmit a signal indicative of the position of sliding attachment ring 70 relative to the rail 68 in the direction of arrow C (FIG. 4A), and sliding attachment ring 70 may include rotational encoders 78, 80 for transmitting signals indicative of a pivotal orientation of the sliding attachment ring 70 in the direction of arrow D (FIG. 4A) and the rotational position of the shaft 46 in the direction of arrow F (FIG. 4A), respectively.

The signals from the encoders 72, 74, 76, 78, 80 all may be transmitted to the computer control 24 (FIG. 1) to give an indication of the orientation of the end effect tool 18 relative to the opening 40. These signals may be processed by the computer control 24 to generate a virtual and/or actual representation 52, 54, respectively, of the object 36 being viewed. The embodiment of FIGS. 4A and 4B may eliminate the need for IMU 22. However, string encoder 26 or LMD 34 still may be necessary to detect the "in-and-out" motion of the shaft 46 of the extended-reach arm 12 relative to the inspection opening 40 in the direction of arrow E (FIG. 4A).

Figure 5A:
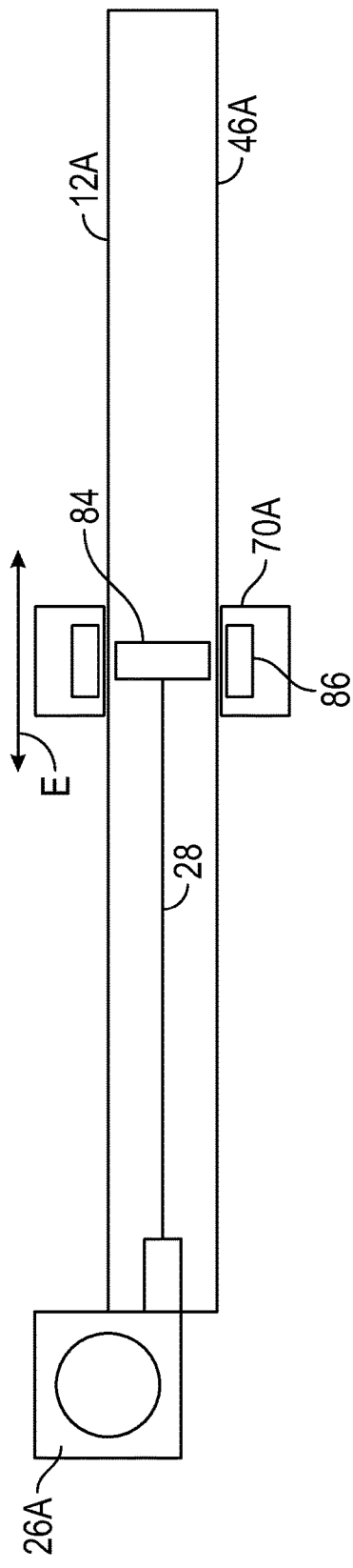
Figure 5B:
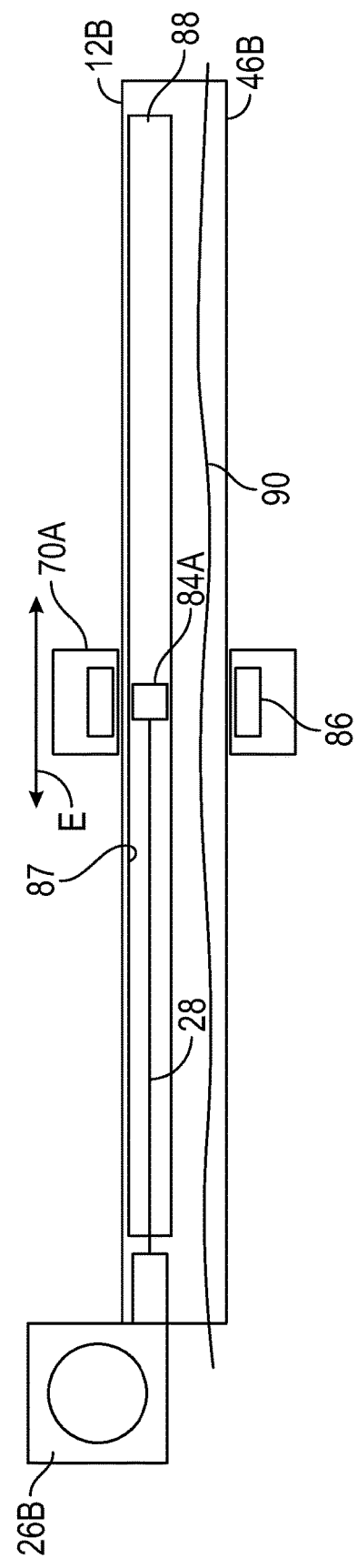

FIGS. 5A, 5B and 5C show different embodiments of the string encoder 26A, 26B, 26C, and sliding attachment ring 70A and 70C that may be used, for example, in the embodiment of FIGS. 4A and 4B to detect motion of the shaft of the extended-reach arm 12 in the direction of arrow E (FIG. 4A). As shown in FIG. 5A, string encoder 26A may include a cable 28 that is attached to a disk 84 that may be of ferromagnetic material, such as steel. The disk 84 may be shaped to be positioned within the hollow interior of the shaft 46A for relative slidable movement.

The sliding attachment ring 70A may include a ring magnet 86. The ring magnet 86 may maintain the metal disk 84 in the position shown in FIG. 5A, namely, at or near the center of the sliding attachment ring 70A. As the shaft 46A of the extended-reach arm 12A is moved longitudinally (i.e., in the direction of arrow E in FIG. 5A) relative to the sliding attachment ring 70A, the metal disk 84 will remain fixed, aligned with the magnet 86 within the sliding attachment ring, causing the cable 28 either to be withdrawn within the string encoder 26A or extended outwardly from it, thus enabling the string encoder 26A to generate a signal indicative of the relative longitudinal position of the shaft 46A to the sliding attachment ring 70A. In an alternate embodiment of FIG. 5A, the sliding attachment ring 70A may include a metal ring 86, and the disk 84 may be made of a ferromagnetic material. With either embodiment, the magnetic attraction between the disk 84 and the ring 86 may maintain the disk in the position shown in FIG. 5A.

As shown in FIG. 5B, the shaft 46B of the extended-reach arm 12B may include a hollow interior that receives a tube 88 that is also hollow, and receives a ring magnet or ferromagnetic disk 84A within it. The tube 88 may be attached to an interior wall 87 of the shaft 46B by an adhesive, bonding or other means. The sliding attachment ring 70A may include a magnet or metal disk (if the disk 84A is comprised of magnetic material) 86. The magnetic attraction between the ring magnet or disk 84A and ring 86 may maintain the magnet or disk 84A in the position shown in FIG. 5B as the shaft 46B is moved longitudinally in the direction of arrow E shown in FIG. 5B relative to sliding attachment ring 70A.

Again, this relative movement may cause the cable 28 either to be drawn into the string encoder 26B or extended from it, thus generating a signal indicative of the relative longitudinal position of the shaft 46B to sliding attachment ring 70A. An advantage of including the hollow tube 88 within the interior of shaft 46B is that clearance may be provided for other wires and cable 90 to extend along the interior. Such wires and cables 90 may include connections to the LMD 34 and/or camera 32 (FIG. 1).

As shown in FIG. 5C, the shaft 46C has a hollow interior that provides a conduit for other wires and cables, generally designated 90, to extend through it. The sliding attachment ring 70C itself may be connected by the cable 28 to the string encoder 26C. Relative longitudinal movement of the shaft 46C of the extended-reach arm 12C in the direction of arrow E may cause the cable 28 to be withdrawn into or extended outwardly from the string encoder 26C, thereby indicating the relative position of the shaft 46C to the sliding attachment ring 70C.

Figure 6:
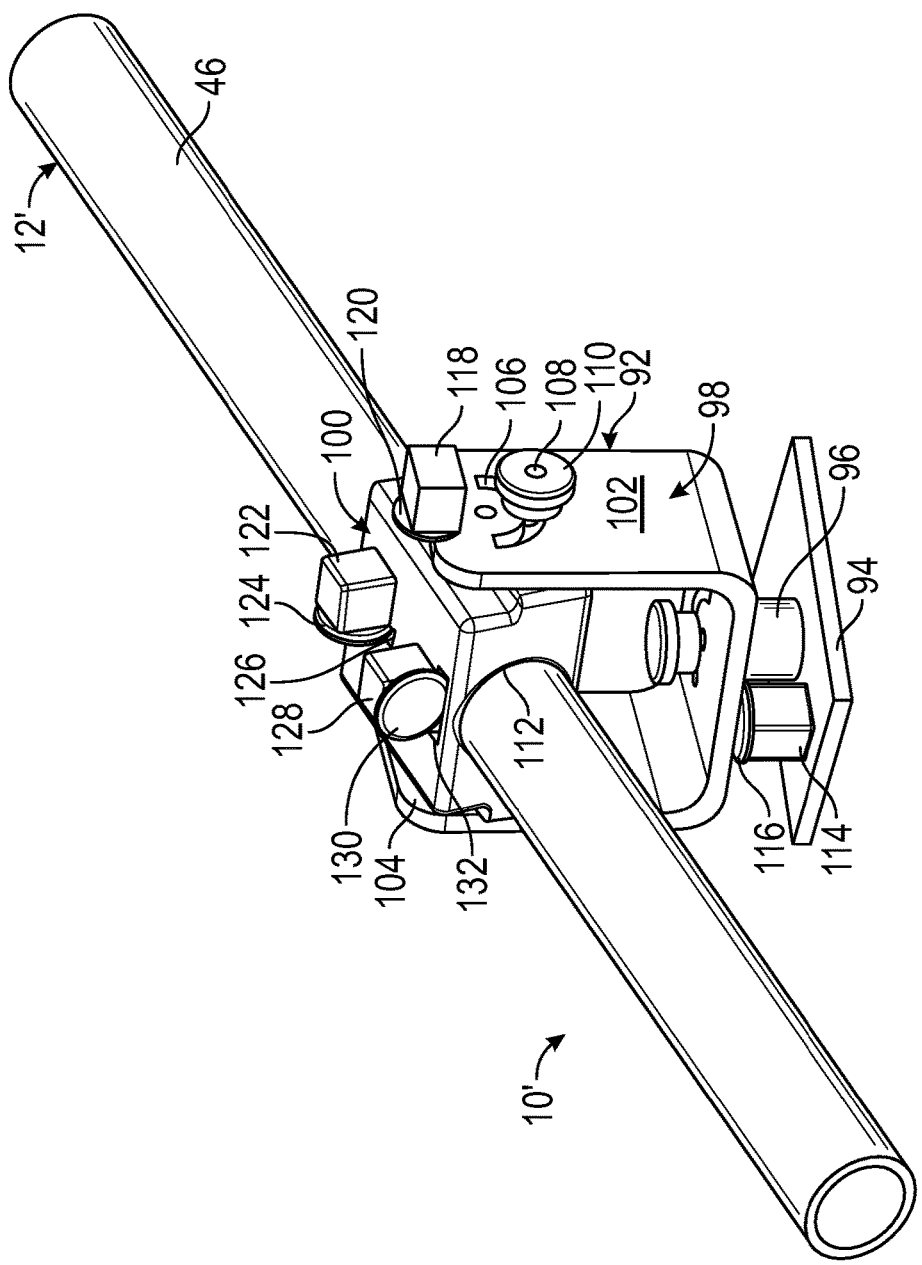
FIG. 6 is yet another embodiment of the disclosed tracking-enabled extended-reach tool system.

In yet another embodiment, shown in FIG. 6, the tracking-enabled multi-axis tool system, generally designated 10', may include a gimbal in the form of a tilt-swivel support system 92 in place of, for example, the IMU 22, encoder 26 and slider ball 30 components of the embodiment of FIG. 1. Tilt-swivel 92 may include a support 94 that may include a stand (not shown) or an attachment (not shown) to wall 42 (FIG. 1). A shaft 96 is pivotally mounted on support 94 and includes a U-shaped bracket 98 so that the shaft and U-shaped bracket swivel relative to the support 94 about a vertical axis as shown in FIG. 6. A block 100 is shaped to fit between and may be pivotally attached to the arms 102, 104 of the U-shaped bracket 98. Arm 102 may include an arcuate slot 106 that receives threaded stud 108 on which a locking knob 110 is mounted to provide an adjustable friction resistance to pivotal movement of the block 100 relative to the bracket 98.

The block 100 may include a bore 112 shaped to slidably and rotationally receive the shaft 46 of the extended-reach arm 12'. A wheel encoder 114 may be mounted on the support 94 and include a wheel 116 that engages shaft 96. Wheel 116 may be oriented to rotate in response to rotation of the shaft 96, and thus encoder 114 may detect swivel movement of U-shaped bracket 98, and thus swivel movement of shaft 46. A wheel encoder 118 may be mounted on arm 112 and include wheel 120 positioned to engage the block 100. Wheel 120 is oriented to rotate in response to pivotal movement of the block, and thus elevational movement of the shaft 46, as it pivots relative to the bracket 98.

A wheel encoder 122 may be mounted on block 100 and include a wheel 124 that extends through a slot 126 in the block to contact shaft 46. Wheel 124 is oriented such that it is rotated in response to longitudinal movement of shaft 46 relative to block 100, and therefore to system 92. A wheel encoder 128 may be mounted on block 100 and include a wheel 130 that extends through slot 132 in block 100 to engage shaft 46. Wheel 130 is oriented such that it rotated in response to rotational movement of the shaft 46 relative to block 100, so that encoder 128 may detect rotational movement of shaft relative to system 92.

Since wheels 124 and 130 are mounted so that they measure different motions (translation and rotation, respectively) of shaft 46, wheels 124 and 130 may be omni wheels that allow the surface on which they are rolling to slide freely in the direction perpendicular to their respective rotation directions.

Encoders 114, 118, 122, and 128 each may be connected to send a signal to computer control 24 (FIG. 1). Consequently, computer control 24 may receive signals indicative of a location of distal end 14 of shaft 46 by calculating the longitudinal, rotational, tilting, and swivel movements of the shaft as measured by encoders 114, 118, 122, and 128.

In operation, a user or operator may input to the computer control 24 identification information pertaining to the aircraft or other enclosure to be inspected, and may input identification indicia of the inspection opening 40. This information may enable the computer control to access the appropriate library of data for the enclosure to be inspected. With the embodiment of FIG. 1, the user may attach the slider ball in position at or near the inspection opening 40. With the embodiment of FIGS. 4A and 4B, the user may attach the slides 56, 58 adjacent to the inspection opening 40. At this point, the user may be positioned on the outside of wall 42 and will not be able to see through the inspection opening 40.

The user then may manipulate the extended-reach arm 12 by grabbing the handle 20, such that the distal end 14 of the shaft 46 passes through the inspection opening 40 and enters the inspection space 44. The user may view an actual or virtual representation on display 38 or 50 of the inspection space 44. The user may manipulate the extended-reach arm 12 so that the camera 32 is oriented to view a desired object 36. With the embodiment of FIG. 1, signals from the IMU 22 and one or both the string encoder 26 and LMD 34 may be utilized by the computer control 24, which converts rotational and linear measurements from the IMU and one or both the string encoder and LMD into spatial location representations for 3-D models, which show the position and orientation of the end effector 18 relative to the inspection opening 40 in real time. The computer control 24 may use kinematic (i.e., mathematical) models of the arm 12, 12' and end effector 18, 218 along with real-time measurement data from the sensors (rotational encoders of the tilt-swivel support system 92 in FIG. 6, or the IMU 22 and string encoder 26 or LMD 27 of the system 10 of FIG. 1) to generate 4×4 homogeneous transformation matrices that define the location of the individual components of the arm and end effector in 3-D space. With the embodiment of FIGS. 4A and 4B, the computer control 24 (FIG. 1) may receive signals from the encoders 72, 74, 76, 78, 80, and string encoder 26 to determine one or both of the location and the orientation of the end effector 18 relative to the inspection opening 40. Thus, the computer control 24 may display the appropriate virtual representation 36' at the appropriate orientation relative to the extended-reach arm 12.

If the object 36 includes a defect 56, the defect may appear on the representation 54. The user may actuate the computer control 24 (which may be by touching a touch screen display) to make a note of the location of the defect 56, and may actuate the computer control to record the representation 54 showing the object 36 and defect 56. Once the inspection is completed, the computer control may generate a report of the representation and/or location of the object 36 and defect 56. The inspection may be facilitated by use of the portable device 24A. The portable device may receive information relating to the relevant aircraft and location of the inspection opening 40, and access stored information (either locally on the device 24A or remotely), and display a representation 38A of the objects being inspected (FIG. 3). This representation may be manipulated by manipulating the spatial orientation of the device 24A to enable a user to visualize the inspection space 44 and the position of the extended-reach arm 12 within it.

Figure 7:
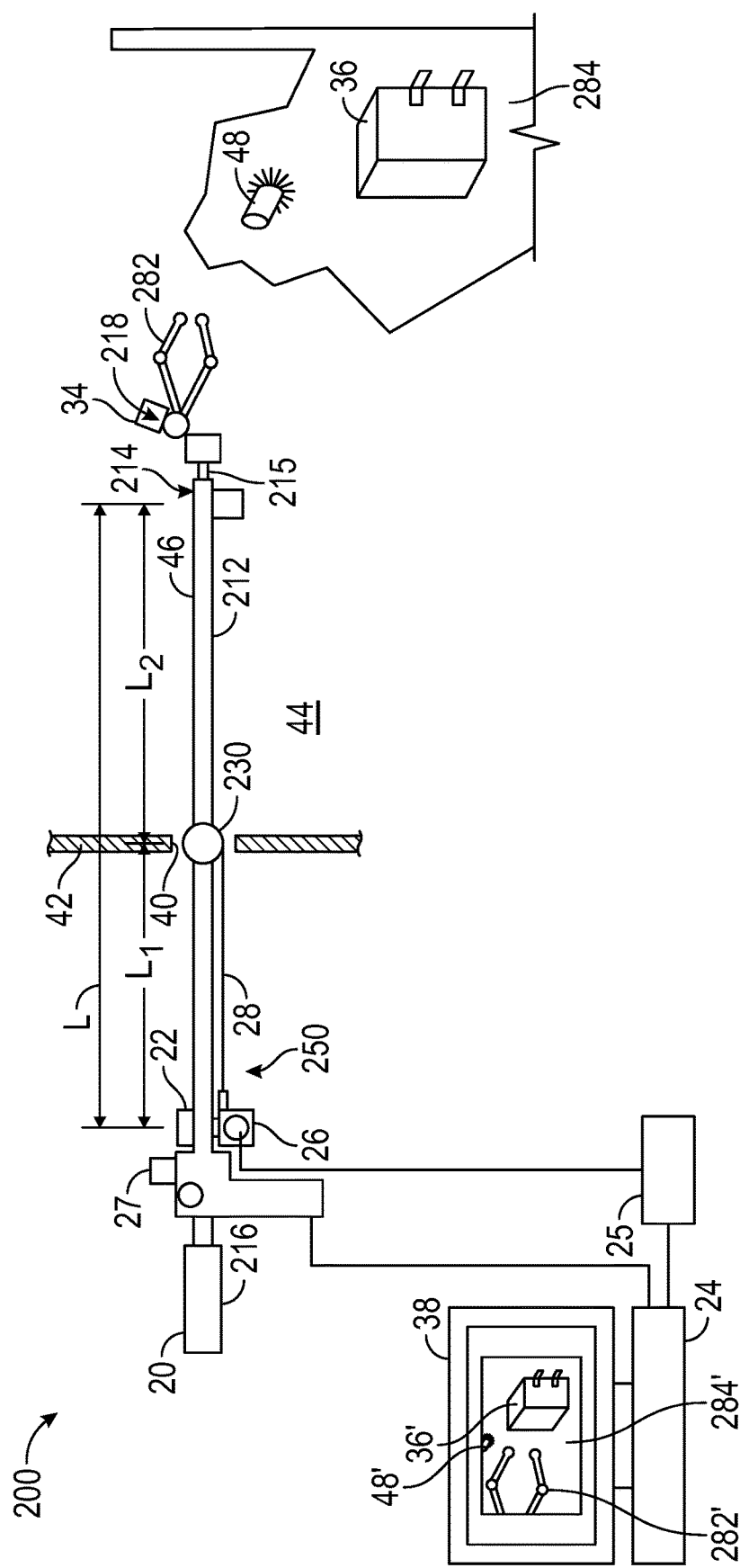
FIG. 7 is still another embodiment of the tracking-enabled extended-reach tool system.

As shown in FIG. 7, tracking-enabled extended-reach tool system, generally designated 200, may include an extended-reach arm 212 having a first end 214 and a second end 216, and an end effector 218 including a tool 282. The tool 282 may be adjacent the first end 214. The extended-reach arm 212 may engage a gimbal 230 for relative rotational movement and relative slidable movement through the opening 40 in the wall 42. The end effector 218 and tool 282 may be positioned on a side of the wall 42 opposite the second end 216. In embodiments, the wall 42 may take the form of a bulkhead or other structure of a vehicle such as an aircraft, a spacecraft, a satellite, a land vehicle including a military vehicle, and/or a marine vehicle including a military marine vehicle. In other embodiments, the wall 42 may be part of a fixed structure, such as an electrical bus.

As with the embodiments of FIGS. 1-6, the gimbal 230 may be part of a sensor system 250 that may include IMU 22, string encoder 26, rotational encoder 74, and LMD 27. The gimbal 230 may take the form of any one of the gimbals of FIGS. 1; 4A and 4B; 5A, 5B, and 5C; and 6 described previously. The sensor system 250 may measure a selected one or more of gimbal 230 and end effector 218 rotations, the linear position of the extended-reach arm 212 relative to the gimbal 230, and a position and spatial orientation of the tool 282 relative to the opening 40. The display 38 is connected to receive representation signals from the computer control 24.

The computer control 24 may be connected to receive rotational and linear measurements from the sensor system 250. The computer control 24 may convert the rotational and linear measurements into spatial location representations for virtual representations 36', 282' of three-dimensional (3-D) models of the workpiece 36 and the tool 282 to determine one or both of a position and an orientation of the tool 282 relative to the opening 40 and the workpiece 36 in real time (i.e., as an operator manipulates the arm 212 to move and actuate the tool 282). The computer control 24 also may adjust the virtual representation 36', 282' of the workpiece 36 and the tool 282 as the extended-reach arm 212 and tool 282 move relative to the workpiece 36 to reflect the real-time orientation of the tool relative to the workpiece. The system 200 may include a display 38 connected to receive representation data from the computer control 24. In embodiments, the display 38 may show a virtual environment 284', which replicates the actual environment 284 of the tool 282 and the workpiece 36. The virtual environment 284' may include one or more of a virtual representation 36' of the workpiece 36 and a virtual representation 282' of the tool 282 in real time.

In embodiments, the computer control 24 may be loaded with a 3-D visualization module, which may take the form of a virtual camera, to create on display 38 a representation of a virtual environment 284' that includes 3-D models 282', 36' of the tool 282 and the workpiece 36 that corresponds to the actual environment 284 of the tool and the workpiece continuously and in real time as the tool 282 is moved by an operator and an operation is performed on the workpiece by the tool 282. Thus, the virtual representation of the workpiece 36 and the virtual representation 282' of the tool 282 are real-time, 3-D virtual representations of the tool 282 and the workpiece 36 relative to each other. The visualization module may include 3-D visualization software such as Blender (Blender Foundation), DesignSpark Mechanical (SpaceClaim, RS Components), Unity (Unity Technologies ApS), Unreal Engine (Epic Games, Inc.), OpenSceneGraph (an application programming interface from OpenSceneGraph), and others.

The computer control 24, with the 3-D visualization module, may receive rotational and linear measurements from the sensor system 250, convert the rotational and the linear measurements into spatial location representations for 3-D models of the workpiece 36 and the tool 282, determine one or both of a position and an orientation of the tool relative to the opening 40 and to the workpiece, and adjust the virtual representations of the 3-D models of the workpiece 36 and the tool 282 as the extended-reach arm 212 and tool 282 are moved by an operator relative to the workpiece, thereby representing a continuous, real-time orientation of the tool relative to the workpiece in the virtual environment 284' shown on display 38.

The computer control 24 may be used by an operator to manipulate the virtual representations 36', 282' of the workpiece 36 and the tool 282, respectively, to provide a plurality of viewpoints of the virtual representations of the workpiece 36 and the tool 282 in real time. For example, an operator may, at the operator's discretion, provide a user input to the computer control 24 to manipulate the virtual representations 48' of at least one object 48 on the display 38.

In embodiments, in response to user input, the computer control 24 may rotate and/or translate the viewpoint of the virtual camera to create the virtual representations 36', 282', 284', or the virtual representations 48' of at least one object 48 on the display 38 in an azimuthal or an elevational direction, or from above or below, or from front or rear, or combinations of the foregoing, in real time, to enable the operator to obtain a clear view of the virtual representations of the tool 282 and the workpiece 36 on the display. Such manipulation may be effected without actually moving the arm 212, end effector 218 or tool 282 within the space 44 relative to the workpiece 36. The IMU 22 (FIG. 7) may provide the rotation information, but other techniques, such as drag/swipe/pinch gesture motions on the touch screen-enabled tablet 24A (see FIG. 3), may be employed. Thus, the computer control 24 may provide a virtual representation 48' of at least one object 48 in relation to the virtual representations 282', 36' of the tool and workpiece in real time on the display 38, which in embodiments may be a 3-D virtual representation.

Also in embodiments, the computer control 24 of the system 200 may be used by an operator to manipulate the viewpoint within the virtual environment shown in the virtual representation 38' of the workpiece to provide an operator-selected one of a plurality of viewpoints of the virtual representation 38' of the workpiece and the tool 282 in real time, unobstructed by the object 48, which may appear as a virtual object 48' on the display 38. This may be effected either by changing the viewpoint of the virtual representations of the tool 282 and workpiece 36 in the virtual environment created by the computer control 24 and viewed on the display 38, or by removing all or a selected portion or portions of the virtual representation of the object 48' shown on the display, thereby providing an unobstructed view of what is behind the object 48, which may be the workpiece 36 and/or the tool 282.

The tracking-enabled extended-reach tool system of FIG. 7 operates as follows. The method begins by positioning the gimbal 230 adjacent an opening 40 in a wall 42. The gimbal 230 is fitted with the extended-reach arm 212. The arm 212 may include a first end 214 and a second end 216, and an end effector 218 including a tool 282 adjacent the first end. The extended-reach arm 212 engages the gimbal 230 for relative rotational movement and relative slidable movement through the opening 40 such that the end effector 218 and tool 282 are positioned on a side of the wall 42 opposite the second end 216.

The linear position of the extended-reach arm 212 is measured relative to the gimbal 230, and a position and spatial orientation of the tool 282 relative to the opening 40, with the sensor system 250. The virtual representations 36', 282' of the spatial orientation of the workpiece 36 and the tool 282, respectively, are displayed on the display 38. The virtual environment 284', which may include the workpiece 36 and tool 282, shown on the display 38 is generated by the computer control 24, which receives signals from the sensor system 250, in embodiments through the encoder reader 25, and the computer control determines one or both of a position and an orientation of the tool 282 relative to the opening 40 and to the workpiece 36. The computer control 24 continuously adjusts the virtual representations 36', 282' of the workpiece 36 and the tool 282, respectively, on the display 38 as the extended-reach arm 212 and tool move relative to the workpiece, for example, when moved by an operator to effect an operation on the workpiece, to reflect a continuous, real-time orientation of the tool relative to the workpiece throughout the operation.

The operator (not shown) of the system 200 may be guided by the real-time display of virtual representations of the tool 282 and workpiece 36 in the virtual environment 284' on the display and move and otherwise manipulate the extended-reach arm 212 to act upon the workpiece 36 with the tool 282 in the environment 284. The operator may grip the handle 20 and actuate the tool 282 with a remote actuator that may be incorporated in the handle 20, or as part of the computer control 24. The action may include an operation on the workpiece 36 in the nature of inspection, maintenance, repair, and/or replacement of the workpiece. The actions of the tool 282 upon the workpiece 36 may be recorded and stored on the computer control 24, and/or remotely. Data concerning the operation, which may include a record of the action of the virtual representation of the tool 282 upon the virtual representation of the workpiece 36, and/or the action of the actual tool 282 upon the actual workpiece 36, which would require the camera 32 on the arm 12 shown in FIG. 1, may be stored in storage on the computer control 24 and/or remotely.

The system 200 described with reference to FIG. 7 may be used with a tool 282 selected from a gripper, a drill, a grinder, a polisher, a stapler, a vacuum, a laser scanner, a laser range meter, a laser scanner, a stereoscopic camera, a depth camera, and a marking device. In other embodiments, the tool 282 may be selected from a pen marker, a sprayer, and an ink-jet print head. These implements may be used to mark the workpiece 36 for further, possibly closer inspection, or later maintenance, repair or replacement.

Figure 8:
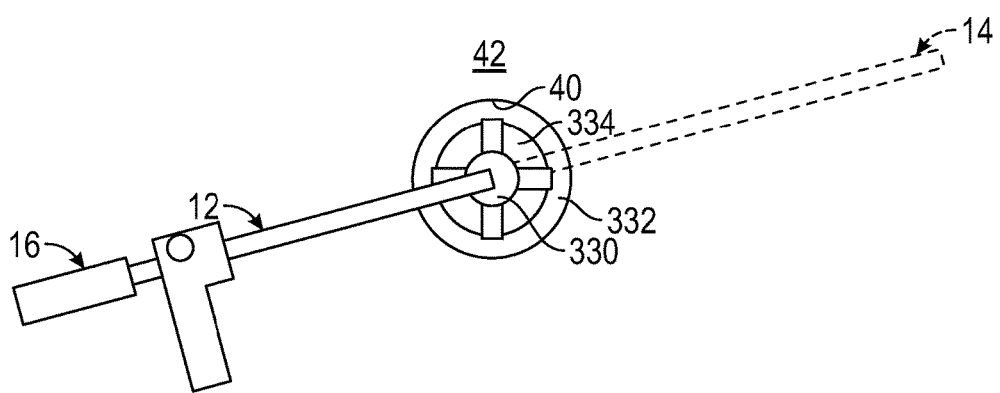
FIG. 8 is a detail of an embodiment of the gimbal of the disclosed tracking-enabled extended-reach tool system.
Figure 9:
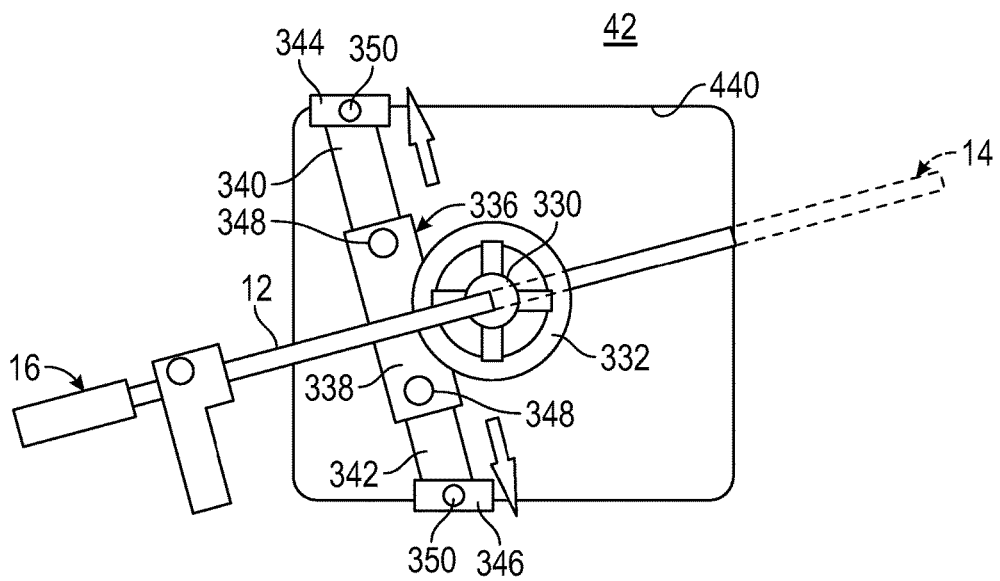
FIG. 9 is a detail of another embodiment of the gimbal of the disclosed tracking-enabled extended-reach tool system.

As shown in FIG. 8, the gimbal 330 may include a mounting ring 332 shaped to engage the contour of the opening 40. The mounting ring 322 may be connected with the ball of the gimbal 330 by one or more spokes 334. In an embodiment, the ball of the gimbal 330 may be centered in the opening 40 in the wall 42. As shown in FIG. 9, the gimbal 330 of FIG. 8 may be mounted in an opening 440 that is not the same size as the mounting ring 332. In this embodiment, the ring 332 may be attached to an adjustable extension 336 shaped to engage and attach to the periphery of the opening 440. The extension 336 may include a sleeve 338 to which the mounting ring 332 is attached. Arms 340, 342 may be slidably received in the sleeve 338, and terminate in U-shaped brackets 344, 346, respectively, shaped to engage the wall 42 at preselected points of the periphery of the opening 440. The arms 340, 342 may be fixed relative to the sleeve 338 by pins, locking mechanisms or set screws 348, and brackets 344, 346 likewise secured to the wall 42 by set screws 350. The adjustable extension 336 may be attached to and removed from the opening 440 as needed.

Figure 10:
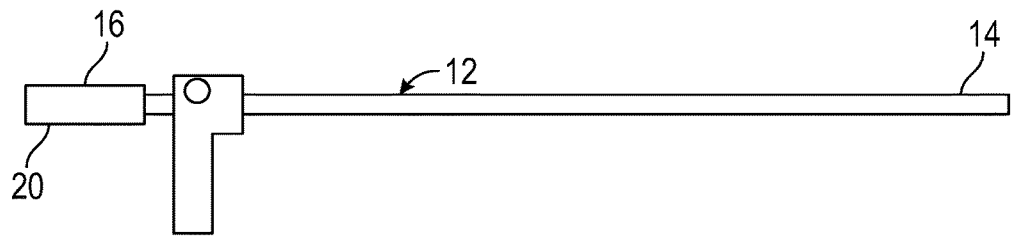
FIG. 10 is a detail showing an embodiment of the extended-reach arm of the disclosed tracking-enabled extended-reach tool system.
Figure 11:
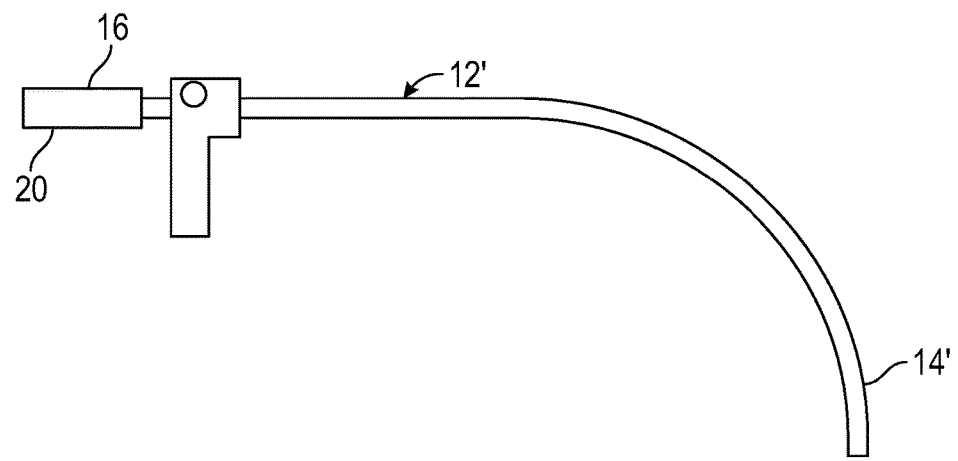
FIG. 11 is a detail showing another embodiment of the extended-reach arm of the disclosed tracking-enabled extended-reach tool system.

As shown in FIGS. 10 and 11, the extended-reach arm 12 may be selected from a rectilinear shape, as shown in FIG. 10, in which the first end 14 is aligned with the handle 20, and an extended-reach arm 12' having a curvilinear shape as shown in FIG. 11, in which the first end 14' is curved and not aligned with the handle 20. In embodiments, the curvature of the arm 12' may be greater or less than that actually shown in FIG. 11. Also in embodiments, the extended reach arm 12 may include telescoping sections, such as telescoping section 215 in FIG. 7. With telescoping section 215, the system 200 may require an LMD 34 to measure the distance of the end effector 218 and tool 282 from the wall 42, the reference object 48, and/or the workpiece 36.

The foregoing embodiments each provide a tracking-enabled, multi-axis, extended-reach tool system 10, 10A, 10B, 10', 200 that can track the position and orientation of the end effector 18, 218 on an extension arm 12, 12A, 12B, 12C, 12', 212 that operates in a confined space. Further, the embodiments 10, 10A, 10B, 10', 200 enable an operator to view a virtual representation of the environment being inspected or worked within from a variety of viewpoints, including the perspective of the end effector 18, 218. This may allow an operator of the tool to have a better situational awareness of the environment 284 in which the end effector 18, 218 operates. In that environment 284, an operator may view, in certain embodiments, 3-D models of all of the components or objects in the environment of interest, as well as view the tool.

This type of interaction with the physical environment of the objects being viewed with virtual representations of the same physical objects may be facilitated by the ability to track one or both of the position and the orientation of the end effector and tool continuously and in real time when registered with the coordinate system of the target object or workpiece. Objects, in some embodiments, may be highlighted in one color to show an operator which items need to be scanned or acted upon, and in another color to show those items that already have been scanned or acted upon. In other embodiments, additional information about the objects and environment may be displayed in a properly registered 3-D context. In still other embodiments, the computer control 24 may generate reports of the operational session of the system 10, 10A, 10B, 10', 200 in which 3-D data points are recorded by the control as a way to confirm that required areas have been scanned.

While the forms of apparatus and methods described herein constitute preferred embodiments of the tracking-enabled multi-axis tool, such apparatus and methods are not exclusive of the inventions covered by this disclosure, and variations may be made therein without departing from the scope of the invention.

What is claimed is:

1. A tracking-enabled extended-reach tool system for acting upon a workpiece, the tool system comprising:
   a gimbal adapted to be positioned adjacent an opening in a surface;
   an extended-reach arm having a first end and a second end, the extended-reach arm further including an end effector including a tool adjacent the first end, the extended-reach arm engaging the gimbal for relative rotational movement and relative slidable movement through the opening such that the end effector and the tool are positioned on a side of the surface opposite the second end;
   a sensor system for measuring gimbal and end effector rotations, measuring a linear position of the extended-reach arm relative to the gimbal, and measuring a position and spatial orientation of the tool relative to the opening;
   a computer control connected to receive rotational and linear measurements from the sensor system, convert the rotational and the linear measurements into spatial location representations for virtual representations of three-dimensional (3-D) models of the workpiece and the tool, determine one or both of a position and an orientation of the tool relative to the opening and to the workpiece, and adjust the virtual representations of the 3-D models of the workpiece and the tool as the extended-reach arm and the tool move relative to the workpiece, thereby representing a real-time orientation of the tool relative to the workpiece; and
   a display for displaying the virtual representations of 3-D models of the workpiece and the tool from the computer control in real time.

2. The tool system of claim 1, wherein the virtual representations of the workpiece and the virtual representations of the tool are real-time, three-dimensional virtual representations of the tool and the workpiece relative to each other.

3. The tool system of claim 1, wherein the computer control includes a three-dimensional visualization module to display three-dimensional models of the tool and the workpiece in a virtual environment corresponding to the actual environment of the tool and the workpiece in real time.

4. The tool system of claim 1, wherein the computer control manipulates a 3-D viewpoint used to create the virtual representations of the workpiece and the tool to provide a plurality of 3-D viewpoints of the virtual representations of the workpiece and the tool in real-time.

5. The tool system of claim 4, wherein the computer control manipulates the virtual representations of the workpiece and the tool to provide the plurality of 3-D viewpoints in response to a user input.

6. The tool system of claim 4, wherein the computer control manipulates the virtual representations of at least one object on the display in response to a user input.

7. The tool system of claim 1, wherein the computer control provides virtual representations of at least one object in relation to the virtual representations of the tool and the workpiece in real-time on the display.

8. The tool system of claim 7, wherein the virtual representations of the at least one object is a 3-D virtual representations on the display.

9. The tool system of claim 7, wherein the computer control manipulates the virtual representations of the workpiece to provide a user-selected one of a plurality of viewpoints of the virtual representations of the workpiece and the tool in real-time unobstructed by the at least one object on the display.

10. The tool system of claim 9, wherein the computer control manipulates the virtual representations of the at least one object by removing part or all of one or more of the at least one object to provide an unobstructed view of the workpiece and/or the tool.

11. A method for acting upon a workpiece with a tracking-enabled extended-reach tool system, the method comprising:
    positioning a gimbal adjacent an opening in a surface;
    engaging the gimbal with an extended-reach arm having a first end and a second end, the extended-reach arm further including an end effector including a tool adjacent the first end, the extended-reach arm engaging the gimbal for relative rotational movement and relative slidable movement through the opening such that the end effector and the tool are positioned on a side of the surface opposite the second end;
    measuring gimbal and end effector rotations, measuring a linear position of the extended-reach arm relative to the gimbal, and measuring a position and spatial orientation of the tool relative to the opening with a sensor system;
    receiving rotational and linear measurements from the sensor system, converting the rotational and the linear measurements into spatial location representations for virtual representations of three-dimensional (3-D) models of the workpiece and the tool, determining one or both of a position and an orientation of the tool relative to the opening and to the workpiece, and adjusting the virtual representations of the 3-D models of the workpiece and the tool as the extended-reach arm and the tool move relative to the workpiece by a computer control, thereby representing a real-time orientation of the tool relative to the workpiece;
    displaying the virtual representations of the 3-D models of the workpiece and the tool from the computer control on a display; and
    manipulating the extended-reach arm to act upon the workpiece with the tool.

* * * * *